United States Patent
Cahan et al.

(10) Patent No.: US 10,441,189 B2
(45) Date of Patent: Oct. 15, 2019

(54) HIGH DEFINITION EEG

(71) Applicant: INTERNATIONAL BUSINESS MACHINES CORPORATION, Armonk, NY (US)

(72) Inventors: Amos Cahan, Ferry, NY (US); Hariklia Deligianni, Alpine, NJ (US); Pei-Yun S. Hsueh, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/969,856

(22) Filed: Dec. 15, 2015

(65) Prior Publication Data
US 2017/0164861 A1 Jun. 15, 2017

(51) Int. Cl.
A61B 5/04 (2006.01)
A61B 5/0478 (2006.01)
A61B 5/00 (2006.01)

(52) U.S. Cl.
CPC .......... *A61B 5/0478* (2013.01); *A61B 5/0006* (2013.01); *A61B 5/6803* (2013.01); *A61B 5/7203* (2013.01); *A61B 5/04004* (2013.01); *A61B 2562/164* (2013.01)

(58) Field of Classification Search
CPC .................................................. A61B 5/04004
See application file for complete search history.

(56) References Cited

U.S. PATENT DOCUMENTS

| | | | | |
|---|---|---|---|---|
| 5,038,782 A * | 8/1991 | Gevins | ................. | A61B 5/0017 600/383 |
| 6,381,481 B1 * | 4/2002 | Levendowski | ...... | A61B 5/0478 600/383 |
| 8,032,209 B2 | 10/2011 | He et al. | | |
| 8,798,707 B2 | 8/2014 | Choi et al. | | |
| 9,037,224 B1 | 5/2015 | Fu | | |
| 2004/0210122 A1 * | 10/2004 | Sieburg | .............. | A61B 5/04085 600/393 |
| 2007/0249952 A1 * | 10/2007 | Rubin | .................. | G04G 15/003 600/544 |
| 2008/0306397 A1 | 12/2008 | Bonmassar et al. | | |

(Continued)

FOREIGN PATENT DOCUMENTS

| | | |
|---|---|---|
| DE | 69025612 T3 | 8/2003 |
| WO | 9817173 | 4/1998 |

OTHER PUBLICATIONS

Moore "Cramming more components onto integrated circuits." Electronics. vol. 38, No. 8, Apr. 19, 1965.*

(Continued)

*Primary Examiner* — Luther Behringer
(74) *Attorney, Agent, or Firm* — Cantor Colburn LLP; Rahan Uddin

(57) ABSTRACT

A method, apparatus and system for measuring electrical activity generated within a brain is disclosed. A headpiece having a first transistor is placed in contact with a head that contains the brain to bring the first transistor into electrical contact with the head. An electronic signal is generated at the first transistor in response to the electrical activity generated within the brain. The electronic signal is processed at the headpiece in order to measure the electrical activity.

4 Claims, 8 Drawing Sheets

(56) References Cited

U.S. PATENT DOCUMENTS

| | | | | |
|---|---|---|---|---|
| 2012/0129301 A1* | 5/2012 | Or-Bach | ............... | G11C 8/16 |
| | | | | 438/129 |
| 2012/0286337 A1* | 11/2012 | Liang | ............. | H01L 21/823431 |
| | | | | 257/288 |
| 2014/0051044 A1* | 2/2014 | Badower | ............... | A61B 5/00 |
| | | | | 434/236 |
| 2015/0380009 A1* | 12/2015 | Chang | .................. | G10L 15/24 |
| | | | | 704/263 |

OTHER PUBLICATIONS

Shaonan et al. "Design of 4-channel Analog Front-ends for Neural Signal Acquisition" 2014 IEEE Workshop on Advanced Research and Technology in Industrial Applications. pp. 1316-1319. Available online Dec. 8, 2014.*

F. Cincotti et al.; "EEG Deblurring Techniques in a Clinical Context", Methods Inf Med Jan. 2004, pp. 114-117 and http://www.cognitiveneuroscience.it.

Myers et al.; "Wearable silver nanowire dry electrodes for electrophysiological sensing", RSC Adv., 2015, 5, DOI: 10.1039/c4ra15101a, pp. 11627-11632.

* cited by examiner

HIGH DEFINITION EEG

BACKGROUND

The present invention relates generally to electroencephalography and, more specifically, to a method and apparatus for improving spatial resolution of electroencephalography.

Electroencephalography (EEG) is the capture of electrical activity generated within the brain. It is currently used as a research tool for deciphering brain functions as well as to diagnose and classify conditions such as epilepsy, narcolepsy and other sleep disorders, organic brain damage, etc. To perform EEG, about 10 to 20 electrodes are placed in electrical contact with the subject's scalp at predetermined locations. The output from the electrodes is expressed as the difference between the potential measured between two electrodes or between an electrode and a reference value. While EEG provides good temporal resolution of electrical activity, spatial resolution of EEG is considered low and other technologies are often used with EEG to improve its spatial resolution.

SUMMARY

Embodiments include a method, apparatus and system for measuring electrical activity generated within a brain. A method includes placing a headpiece having a first transistor in contact with a head that contains the brain to bring the first transistor into electrical contact with the head; generating, at the first transistor, an electronic signal in response to the electrical activity generated within the brain; and processing the signal at the headpiece to measure the electrical activity.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments of the present invention include systems, methods and apparatuses used in electroencephalography (EEG) for obtaining measurements of electrical activity within a brain with a high level of resolution. The apparatus can include a plurality of small electrodes (e.g., microelectrodes), a power source and computation means that are integrated into a headpiece or cap that is applied to a head of a subject. The headpiece can be in communication with a remote computer via a wired connection or a wireless connection. The position in space of each electrode can be mapped in relation to each other electrode or in relation to a landmark, generally an anatomical landmark. The electrodes are mounted to the cap so that their relative positions are fixed. The electrodes are part of an integrated circuit on a flexible substrate that forms the cap. The integrated circuit can include transistors which can be unipolar or bipolar or a combination thereof. Data obtained from EEG can be use with data obtained through other brain diagnostic tests (e.g., magnetic resonance imaging (MRI), functional MRI (fMRI), computed tomography (CT), positron emission tomography (PET), etc.) in order to relate the electrical activity to specific brain structures. During EEG tests performed using the apparatus disclosed herein, the subject can be exposed to different stimuli or made to execute different tasks. The cap and electrodes can be applied to the subject without the need to cut or shave the subject's hair. EEG readings at different points in time can be compared to each other to obtain temporal EEG data. EEG data from one subject can be compared to EEG data from another subject to detect differences in brain activity, especially to detect differences that can correlate with clinical or genetic variations or abnormalities.

Figure 1:
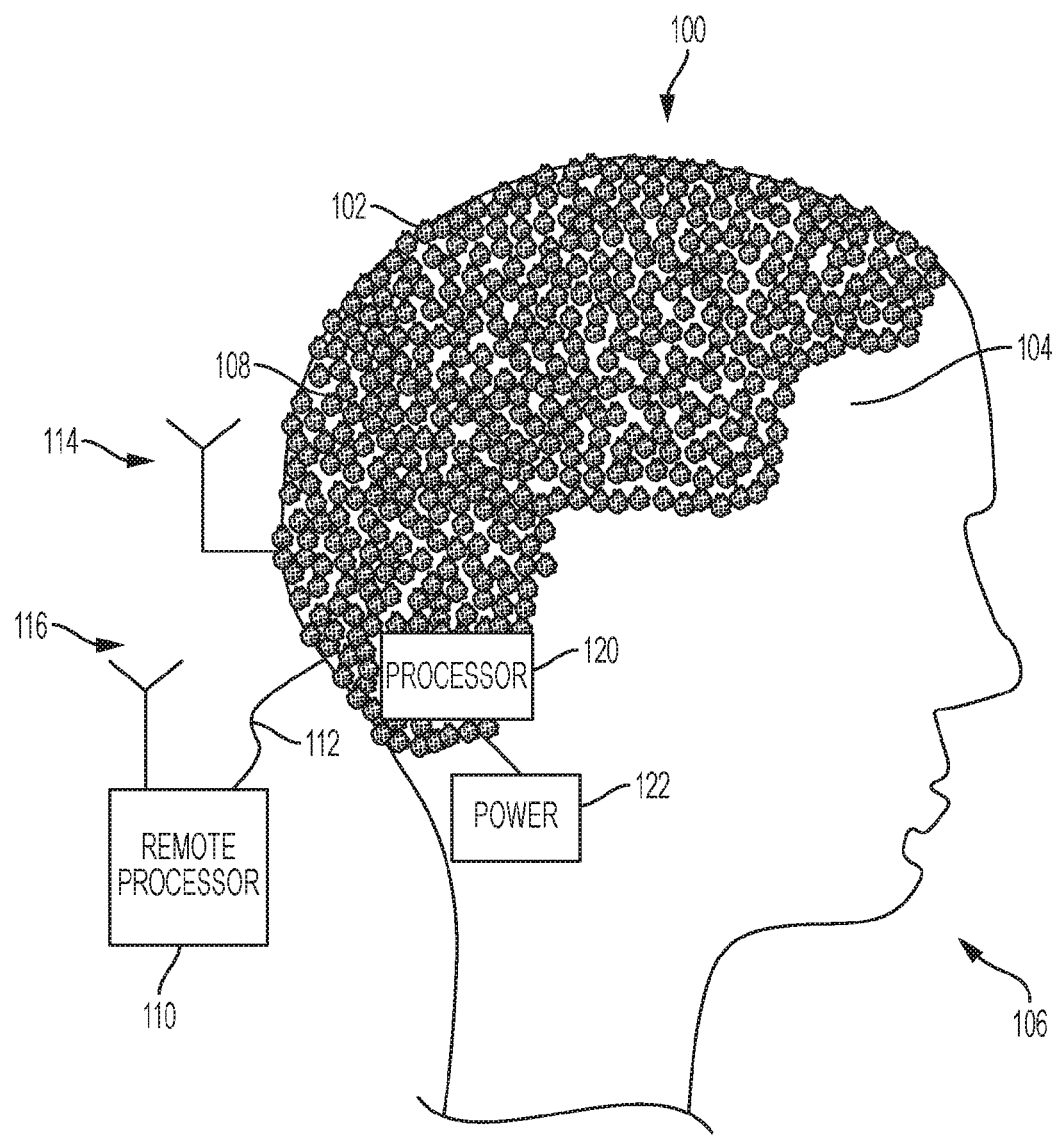
FIG. 1 shows an electroencephalography (EEG) device in one embodiment of the present invention.

Turning now to FIG. 1, an EEG device 100 is shown in one embodiment of the present invention. The EEG device 100 includes a cap or headpiece 102 that is fit over a head or scalp 104 of a subject 106. The headpiece 102 includes a plurality of electrodes 108 that come into contact with the scalp 104 when the headpiece 102 is applied to the scalp 104. The electrodes 108 can include transistors that can be formed on a micro-scale or on a nano-scale. Therefore, the number of electrodes 108 that can be in the headpiece 102 can be in the hundreds or even thousands. For a headpiece 102 with a thousand or more electrodes 108, a spatial resolution of less than 1 centimeter can be achieved. In various embodiments, the subject 106 can wear the headpiece 102 and valid EEG data can be obtained without having to shave or cut the subject's hair. A processor 120 and a power supply 122 can be integrated into the headpiece 102. The headpiece 102 can communicate data to a remote computer or processor 110 either through a wired connection 112 or via a communication channel established using a wireless transmitter 114 and a wireless receiver 116.

Figure 2:
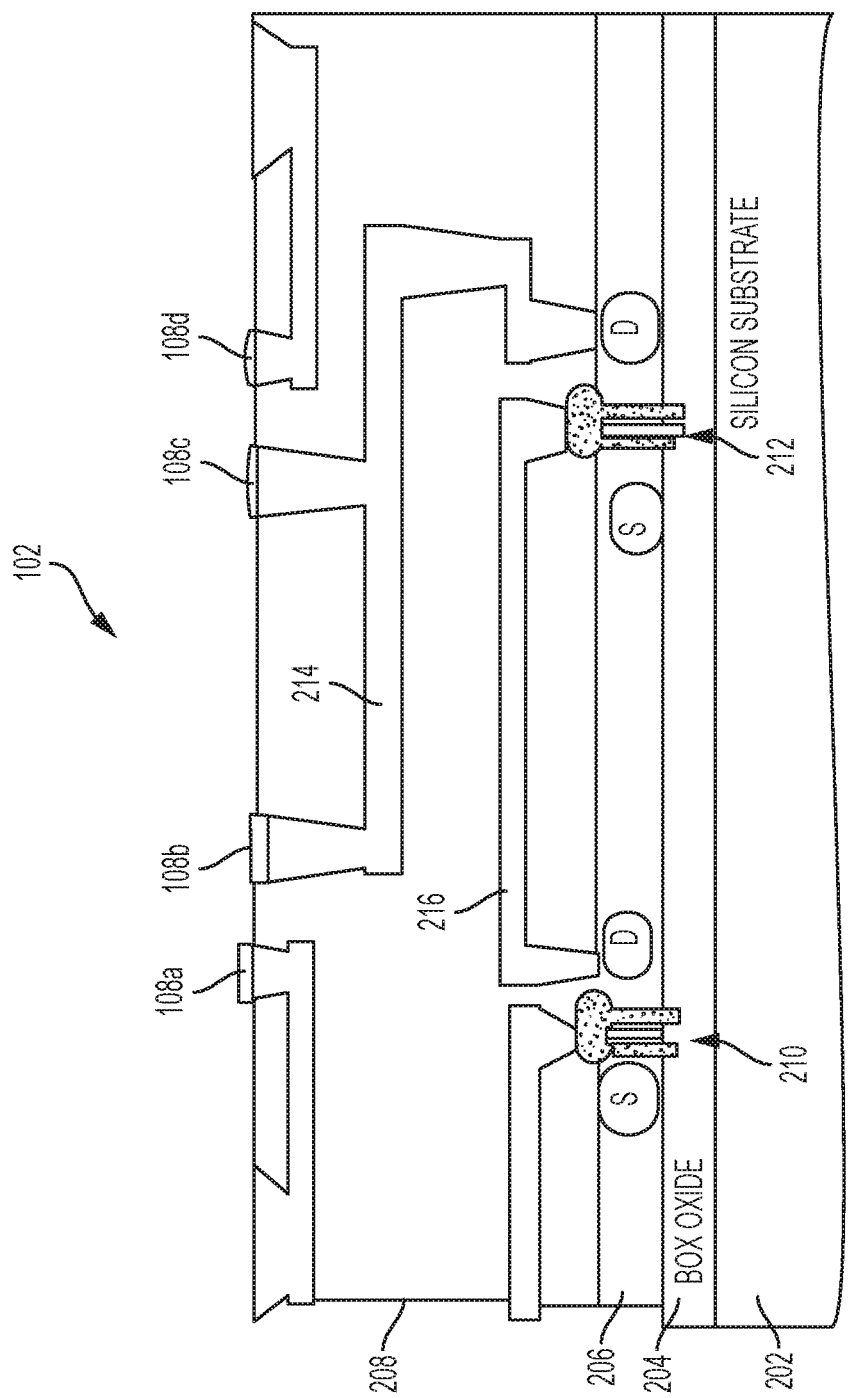
FIG. 2 shows a cross-section of the headpiece of FIG. 1.

FIG. 2 shows a cross-section of the headpiece 102 of FIG. 1. The headpiece 102 is made of a flexible substrate 202 that can be arranged, stretched or molded to fit to or conform to the shape of the scalp 104 of the subject 106. In one embodiment, the substrate 202 can be made of silicon that is from about 100 microns thick to about 700 microns thick and which uses (111) planes of silicon. The thinner the substrate 202, the more flexible the substrate 202 becomes. A buried oxide (BOX) layer 204 is formed on the substrate 202 and an integrated circuit 206 is formed on the BOX layer 204 so as to form a flexible integrated circuit 206. The integrated circuit 206 may include a plurality of transistors. Two transistors 210 and 212 are shown in the integrated circuit 206 for illustrative purposes. In one embodiment of the present invention, transistors 210 and 212 are FinFETs (Fin-Field Effect Transistors) which have a three-dimensional structure.

In the illustrative embodiment of FIG. 2, an insulating layer 208 separates the integrated circuit 206 from electrodes 108a-108d. The electrodes 108a-108d extend above a surface of the insulating layer 208 so as to more easily come into contact with the scalp 104 when the headpiece 102 is applied to the scalp 104. The electrodes 108a-108d can be arranged in any suitable array or pattern. The relative locations of the electrodes 108a-108d and the distances between them are fixed and the separation distances between electrodes (and electrode locations) can be recorded and used when processing the electrical signals in order to help measure the generated electrical activity within the brain and to provide a resolution to the measurements of the electrical activity.

In the illustrative embodiment, electrodes 108b and 108c are connected to transistor 212 through via 214 that passes through the insulating layer 208. However, the number of electrodes connected to via 214 is illustrative only and is not meant to be a limitation of the invention. While via 214 connects to the drain of transistor 212, the via 214 can connect to a transistor gate or a transistor source in alternate embodiments. In various embodiments, transistors 210 and 212 can connect to each other. As shown in FIG. 2, the gate of transistor 212 is connected to drain of transistor 210 through via 216. Other configurations for connecting transistors 210 and 212 are also possible in alternate embodiments. Electrical activity in the brain detected by electrodes 108b and 108c affects operation of transistor 212 in order to generate a current or an electrical signal in the integrated circuit 206. The transistors 210 and 212 can provide electronic signals to the processor (120, FIG. 1). The processor 120 may be an electronic component that is formed within the integrated circuit 206.

Figure 3:
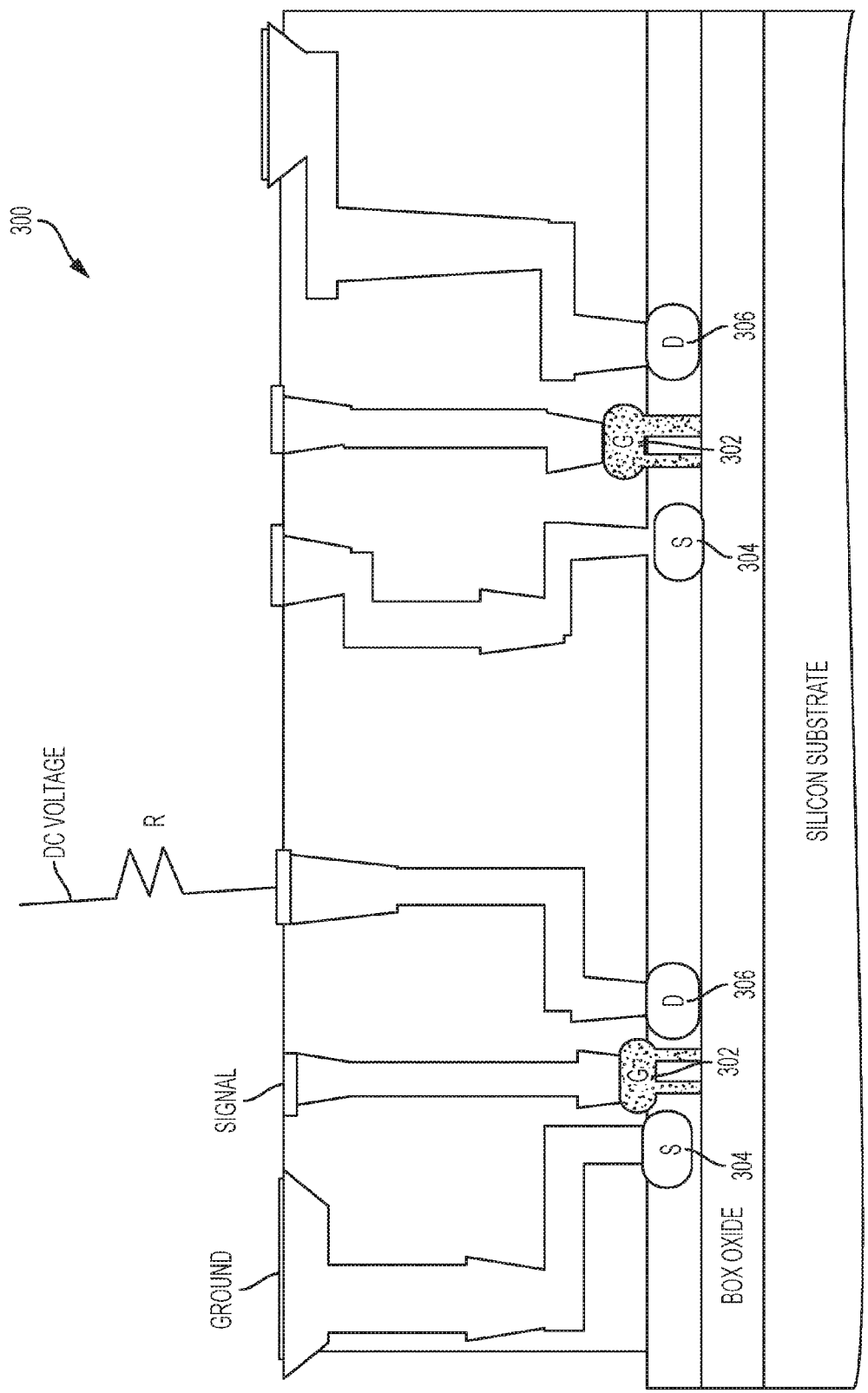
FIG. 3 shows a schematic of a cross-section of an integrated circuit with FinFETs and contact pads in one embodiment of the present invention.

FIG. 3 shows a schematic of a cross-section of an integrated circuit 300 with FinFETs and contact pads in one embodiment of the present invention. A gate 302 controls the flow of electrons between a source 304 and a drain 306. In an n-type FinFET, (positive) current enters through the drain 306 and leaves through the source 304. In a p-type FinFET, (positive) current enters through the source 304 and leaves through the drain 306. The transconductance of the transistor is proportional to the square root of the drain current while in saturation. The transconductance of a circuit controls the gain of the transistor. As a result, a high transconductance is suitable for use in an amplifier circuit. In this circuit 300, the source 304 is connected to ground, with a resistor connected between a DC voltage and the drain 306, and a signal is supplied to the gate 302. The output of the transistor is taken between the drain 306 and the resistor. Large resistors can be used when the transconductance of the transistor is small.

Figure 4:
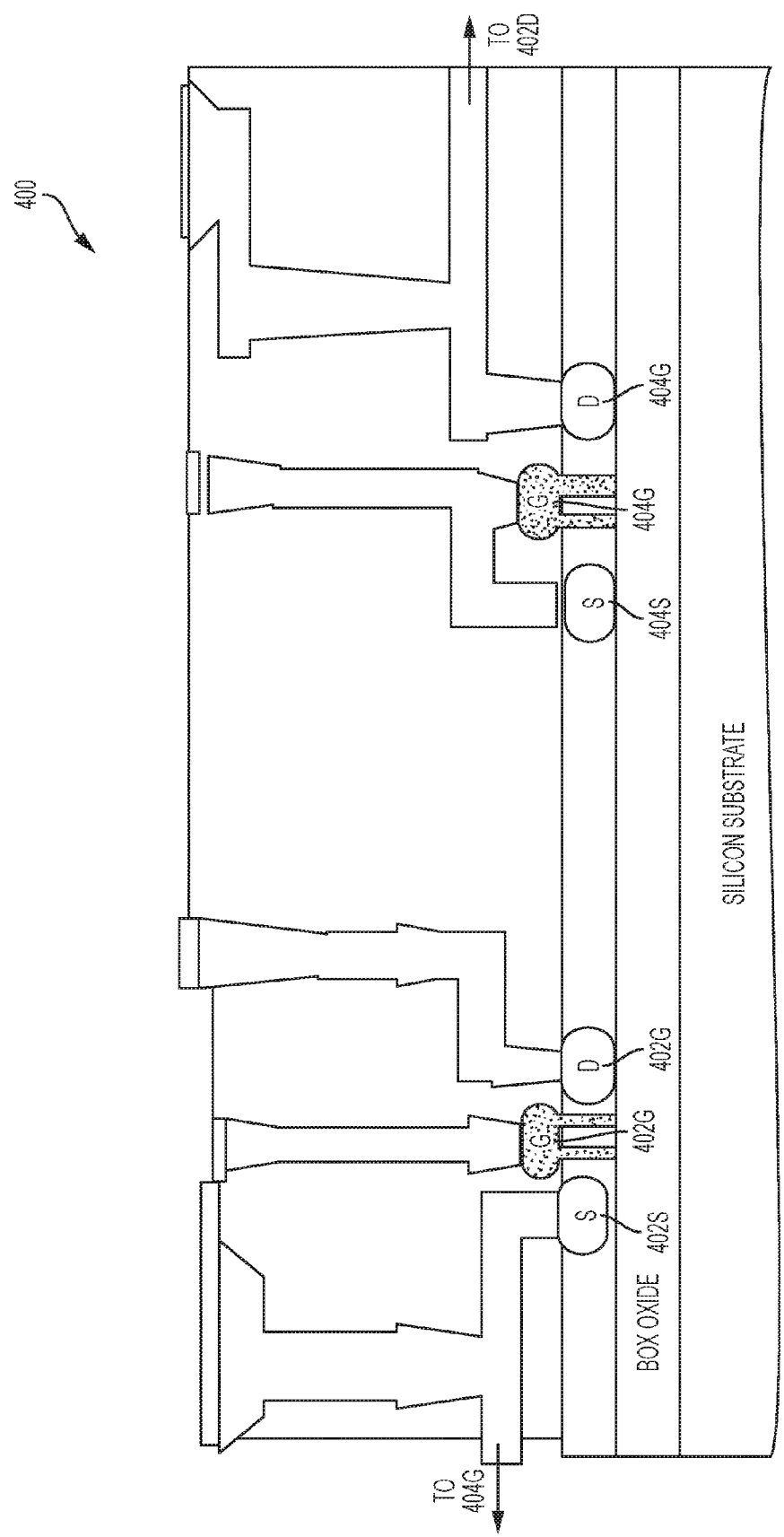
FIG. 4. shows a schematic of a cross section of an integrated with FinFET and contact pads connected as a source follower in one embodiment of the present invention.

FIG. 4 shows a schematic of a cross section of an integrated circuit 400 with FinFET and contact pads connected as a source follower in one embodiment of the present invention. A source follower is a circuit used in measuring signals. Source followers use two transistors (402, 404). A gate 404G of the second transistor 404 is connected to the source 404S of the second transistor 404. The drain 404D of the second transistor 404 is connected to the source 402S of the first transistor 402. This configuration functions like a unity-gain buffer and provides a gain of approximately 1 volt per volt while converting a high impedance to a low impedance. This impedance conversion allows readings to be taken without changing the output resistance of the circuit 400.

Figure 5:
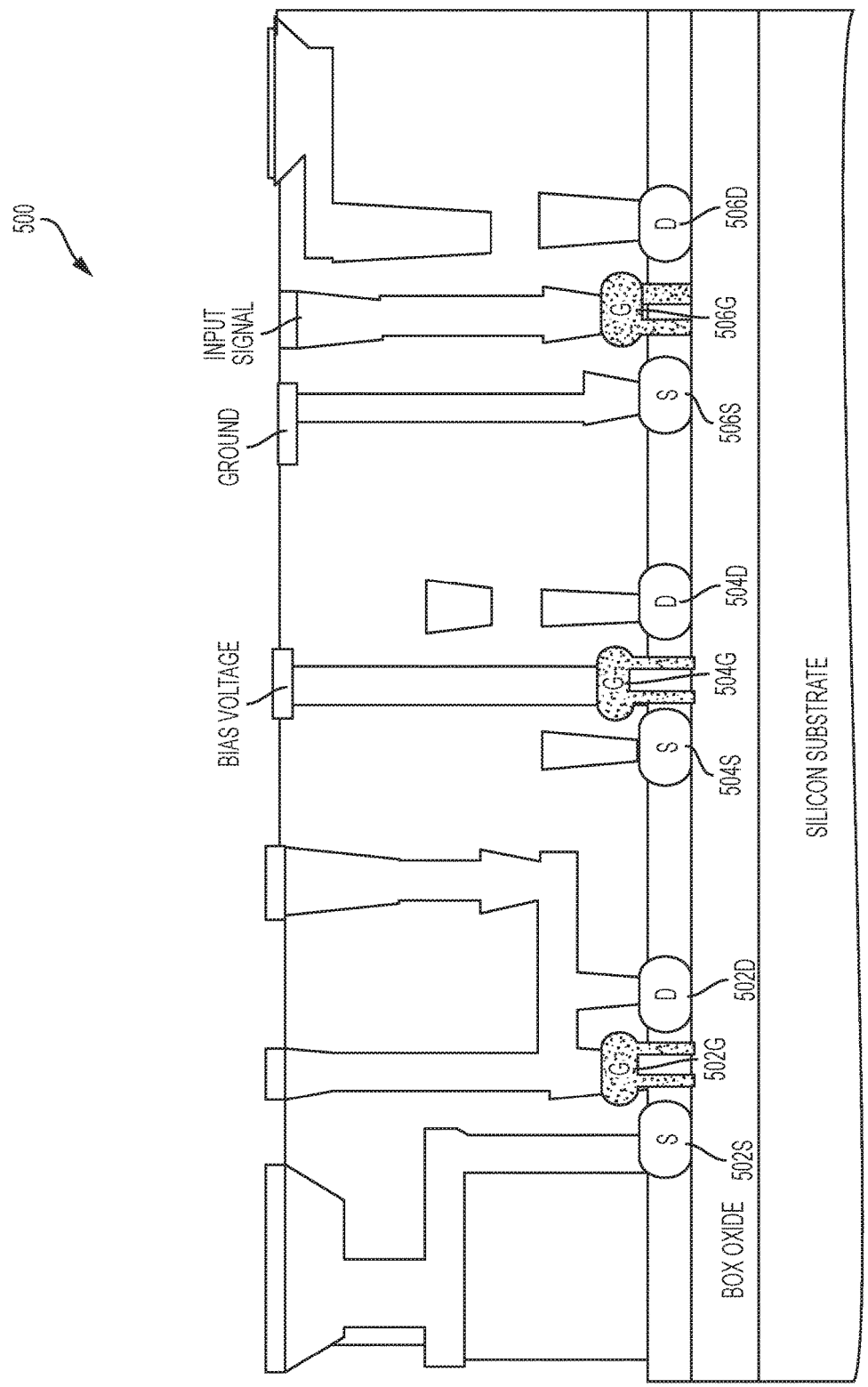
FIG. 5 shows a cascode circuit in one embodiment of the present invention.

FIG. 5 shows a cascode circuit 500 in one embodiment of the present invention. A cascode circuit 500 is a circuit used for the amplification of signals. The cascode 500 includes three transistors. The first transistor 502 has its drain 502D connected to its gate 502G and functions as a resistor. The second transistor 504 has its drain 504D connected to the source 502S of the first transistor 502. The output of the cascode circuit 500 is measured at the drain 504D. The gate 504G of the second transistor 504 is supplied with a bias voltage and the source 504S of the second transistor 504 is connected to the drain 506D of the third transistor 506. The third transistor 506 has its drain 506G connected to the source 504S of the second transistor 504 and receives an input signal at the gate 506G. The source 506S of the third transistor 506 is connected to ground. The cascode circuit 500 has the characteristic of increased frequency response.

Figure 6:
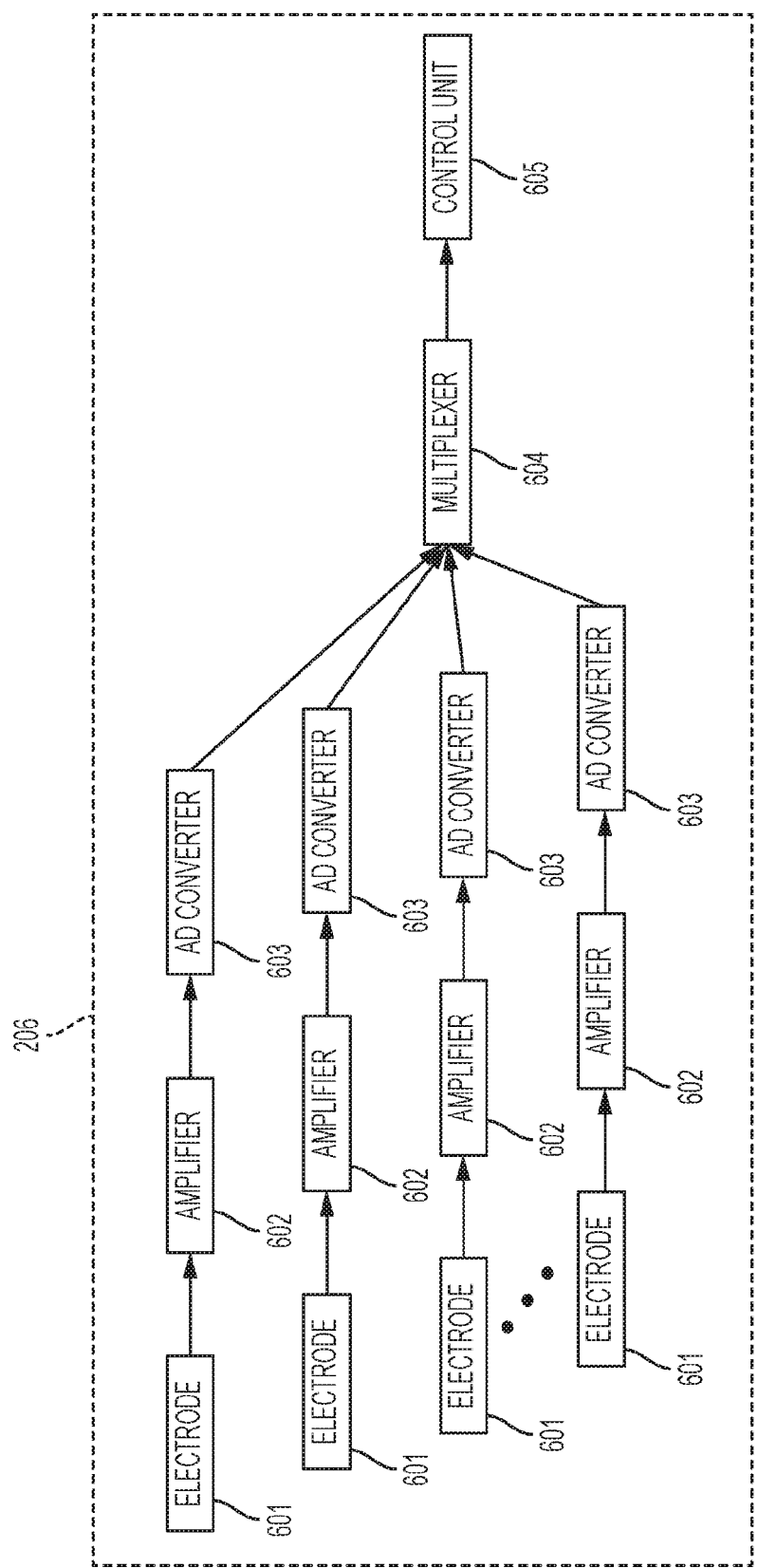
FIG. 6 shows a schematic diagram of an electronic system disposed on the headpiece for providing an EEG signal in response to electrical activity within a brain.

FIG. 6 shows a schematic diagram of an electronic system disposed on the headpiece 102 for providing an EEG signal in response to electrical activity within the brain. Electrodes 601 are used to obtain electrical signals from the brain of the subject. The electrical signals are then sent through amplifiers 602, which can include some of the integrated circuits of FIGS. 2-5. The amplified signal is then sent to an analog-to-digital converter (AD converter) 603 to digitized the signal. The digital signals from multiple AD converters 603 can then be multiplexed at multiplexer 604. The multiplexed signal can then be sent to a control unit 605 which includes a processor for diagnosis and analysis of the electrical activity of the brain. The electrodes 601, amplifiers 602, AD converters 603, multiplexers 604 and control unit 605 can be elements of the integrated circuit 206.

Figure 7:
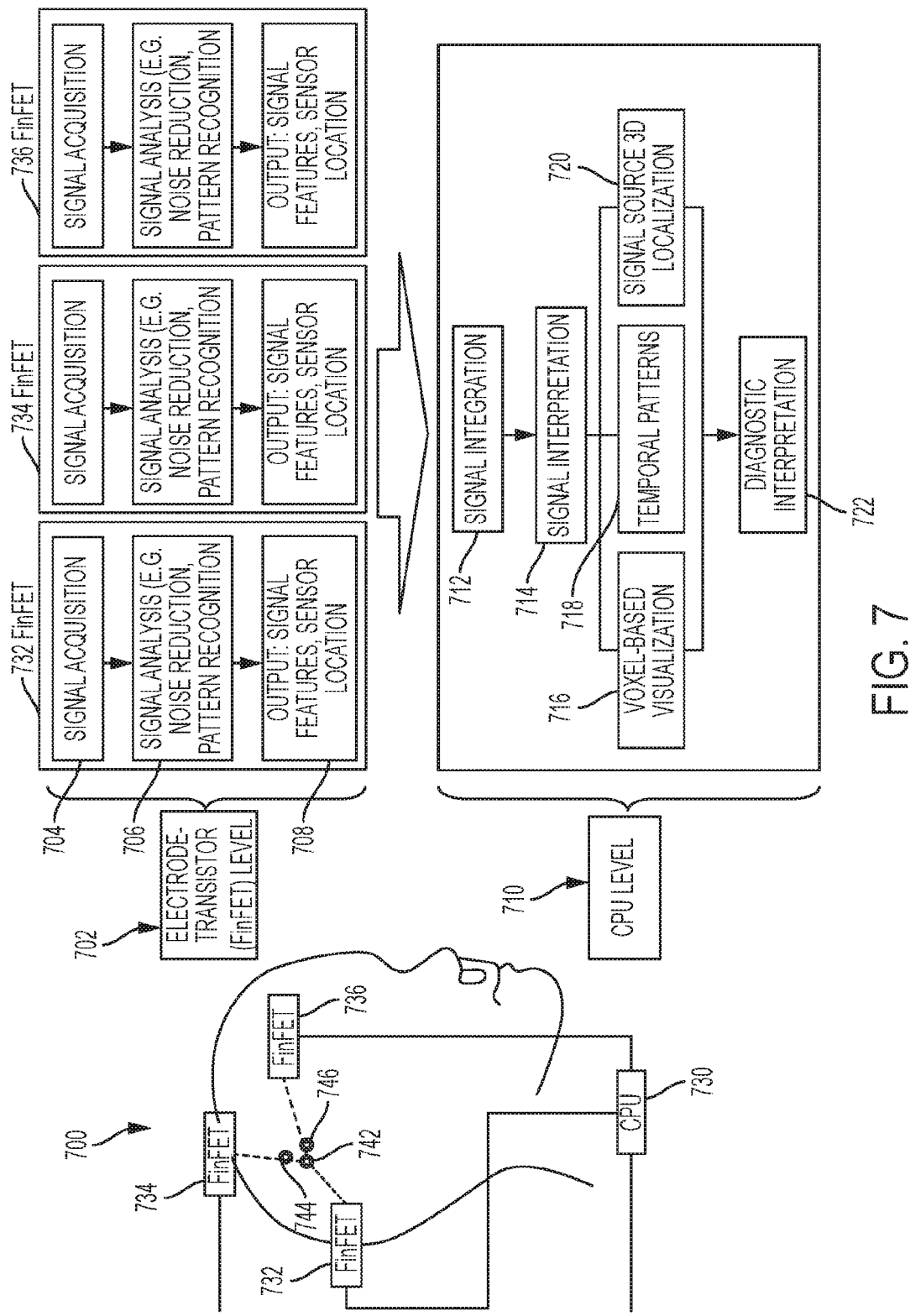
FIG. 7 shows a schematic diagram illustrating a separation of computational assignments within the EEG device.

FIG. 7 shows a schematic diagram 700 illustrating a division of computational labor within the EEG device 100 to those computations 702 performed at the electrode-transistor level and those computations 710 that are performed at the processor level. Three FinFETs 732, 734 and 736 are shown for illustrative purposes connected to electrodes 742, 744 and 746, respectively, and receiving electronic signals from the electrodes 742, 744, 746 in response to electrical activity with the brain. The FinFETs 732, 734 and 736 perform the various computations 702 at the transistor level and sends processed electronic signals to processor 730 of the headpiece 102 for further processing. The FinFETs 732, 734, 736 perform signal acquisition 704, and signal analysis 706 which can include noise reduction and pattern recognition, for example. The FinFETs can then provide an output 708 to the processor 730 that includes, among other things, signal features and signal locations.

The processor 730 receives the output from the multiple FinFETs and performs the processor-level computations 710 starting with signal integration 712. The integrated signal can then be use to generate a signal interpretation 714. The signal interpretation 714 can be used to generate a voxel-based visualization 716 of electrical activity within the brain. The signal interpretation can also be used to gain an understanding of temporal patterns 718 of the electrical activity within the brain. Additionally, the signal interpretation can be used to localize in three-dimensions a signal source 720, i.e., a source of electrical activity in the brain. The various visualizations (i.e., voxel-based visualization 716, temporal patterns 718 and locations of signal source 720) can be used at the diagnostic level 722 by a doctor or researcher. The processor 730 can be integrated into the headpiece 102.

Figure 8:
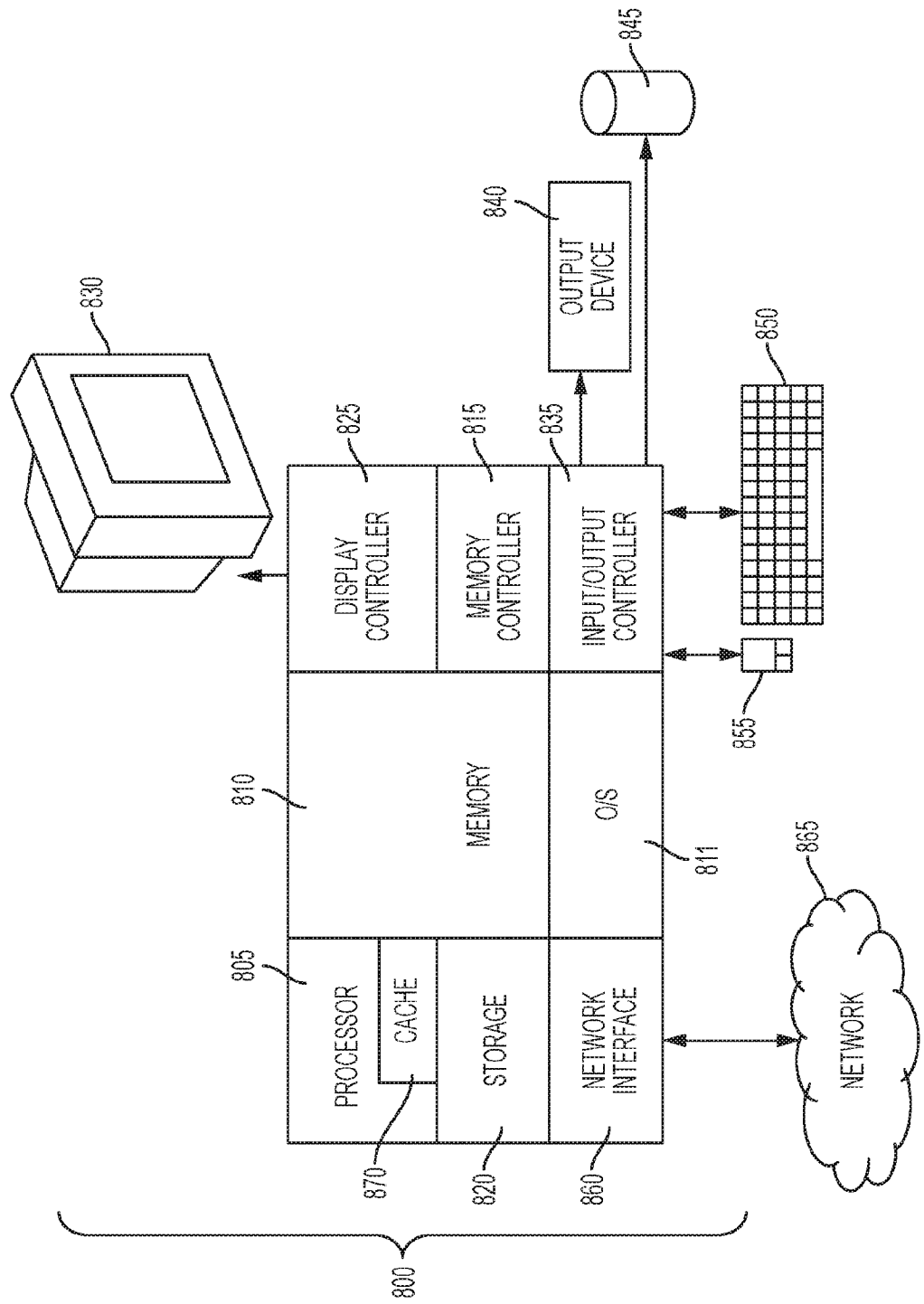
FIG. 8 illustrates a block diagram of a computer system for use in implementing a system or method according to some embodiments.

FIG. 8 illustrates a block diagram of a computer system 800 for use in implementing a system or method according to some embodiments. The systems and methods described herein may be implemented in hardware, software (e.g., firmware), or a combination thereof. In some embodiments, the methods described may be implemented, at least in part, in hardware and may be part of the microprocessor of a special or general-purpose computer system 800, such as a personal computer, workstation, minicomputer, or mainframe computer.

In some embodiments, as shown in FIG. 8, the computer system 800 includes a processor 805, memory 810 coupled to a memory controller 815, and one or more input devices 845 and/or output devices 840, such as peripherals, that are communicatively coupled via a local I/O controller 835. These devices 840 and 845 may include, for example, a printer, a scanner, a microphone, and the like. Input devices such as a conventional keyboard 850 and mouse 855 may be coupled to the I/O controller 835. The I/O controller 835 may be, for example, one or more buses or other wired or wireless connections, as are known in the art. The I/O controller 835 may have additional elements, which are omitted for simplicity, such as controllers, buffers (caches), drivers, repeaters, and receivers, to enable communications.

The I/O devices 840, 845 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 805 is a hardware device for executing hardware instructions or software, particularly those stored in memory 810. The processor 805 may be a custom made or commercially available processor, a central processing unit (CPU), an auxiliary processor among several processors associated with the computer system 800, a semiconductor based microprocessor (in the form of a microchip or chip set), a macroprocessor, or other device for executing instructions. The processor 505 includes a cache 870, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 870 may be organized as a hierarchy of more cache levels (L1, L2, etc.).

The memory 810 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 810 may incorporate electronic, magnetic, optical, or other types of storage media. Note that the memory 810 may have a distributed architecture, where various components are situated remote from one another but may be accessed by the processor 805.

The instructions in memory 810 may include one or more separate programs, each of which comprises an ordered listing of executable instructions for implementing logical functions. In the example of FIG. 8, the instructions in the memory 810 include a suitable operating system (OS) 811. The operating system 811 essentially may control the execution of other computer programs and provides scheduling, input-output control, file and data management, memory management, and communication control and related services.

Additional data, including, for example, instructions for the processor 805 or other retrievable information, may be stored in storage 820, which may be a storage device such as a hard disk drive or solid state drive. The stored instructions in memory 810 or in storage 820 may include those enabling the processor to execute one or more aspects of the systems and methods of this disclosure.

The computer system 800 may further include a display controller 825 coupled to a display 830. In some embodiments, the computer system 800 may further include a network interface 860 for coupling to a network 865. The network 865 may be an IP-based network for communication between the computer system 800 and an external server, client and the like via a broadband connection. The network 865 transmits and receives data between the computer system 800 and external systems. In some embodiments, the network 865 may be a managed IP network administered by a service provider. The network 865 may be implemented in a wireless fashion, e.g., using wireless protocols and technologies, such as WiFi, WiMax, etc. The network 865 may also be a packet-switched network such as a local area network, wide area network, metropolitan area network, the Internet, or other similar type of network environment. The network 865 may be a fixed wireless network, a wireless local area network (LAN), a wireless wide area network (WAN) a personal area network (PAN), a virtual private network (VPN), intranet or other suitable network system and may include equipment for receiving and transmitting signals.

Systems and methods according to this disclosure may be embodied, in whole or in part, in computer program products or in computer systems 800, such as that illustrated in FIG. 8.

Technical effects and benefits of some embodiments include providing multiple buffers between two parties within a single conversation. Embodiments enable interrupting one conversational topic with another conversational topic with minimum of command entries from the user into her communication device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for measuring electrical activity generated within a brain, the apparatus comprising:
    a headpiece including a stretchable substrate,
    an integrated circuit formed on the stretchable substrate,
    an insulating layer formed on the integrated circuit,
    a plurality of electrodes arranged on a surface of the insulating layer, the plurality of electrodes configured with fixed relative positions to provide a spatial resolution of less than 1 centimeter over the brain,
    a plurality of vias extending through the insulating layer, each of the plurality of vias connecting the integrated circuit to an electrode of the plurality of electrodes, wherein the headpiece is placed in contact with a head that contains the brain to conform the substrate and integrated circuit to the shape of the head to bring the plurality of electrodes into contact with the head, wherein the integrated circuit includes:
        a plurality of FinFETs that perform signal acquisition, signal analysis, noise reduction and pattern recognition, and
        a processor that receives signal features and sensor locations from the plurality of FinFETs and provides a diagnostic interpretation based on the electrical activity in the brain; and
    a remote processor for receiving the diagnostic interpretation from the processor and showing the diagnostic interpretation at a display.

2. The system of claim 1, wherein the integrated circuit conforms to a shape of the head in order to bring the plurality of electrodes into contact with the head.

3. The system of claim 1, wherein a second electrode is at a fixed separation distance from a first electrode and the processor processes the electrical signal using the fixed distance.

4. The system of claim 1, wherein the headpiece further comprises a wireless transmitter for transmitting data to the remote processor.

* * * * *